United States Patent
Jarl

Patent Number: 5,692,926
Date of Patent: Dec. 2, 1997

[54] ELECTRODE CONTACT DEVICE, PARTICULARLY AN ELECTRODE CONTACT HEAD, AND AN ELECTRODE ATTACHMENT DEVICE FOR AN ELECTRODE CABLE OF A CARDIAC PACEMAKER, AND A METHOD FOR PRODUCING SUCH AN ELECTRODE CONTACT DEVICE

[75] Inventor: Per Erik Jarl, Järfälla, Sweden

[73] Assignee: Pacesetter AB, Solna, Sweden

[21] Appl. No.: 600,486

[22] Filed: Feb. 13, 1996

[30] Foreign Application Priority Data

Feb. 20, 1995 [SE] Sweden .................. 9500618

[51] Int. Cl.⁶ ........................... H01R 17/18
[52] U.S. Cl. ............... 439/668; 439/909; 128/642; 607/119
[58] Field of Search .................. 439/668, 909; 607/116, 119; 128/642

[56] References Cited

U.S. PATENT DOCUMENTS

| | | | |
|---|---|---|---|
| 3,911,928 | 10/1975 | Lagergren | 128/418 |
| 4,135,518 | 1/1979 | Dutcher | 128/642 |
| 4,387,727 | 6/1983 | Sandstrom | 607/116 |
| 4,514,589 | 4/1985 | Aldinger et al. | 607/119 |
| 4,760,852 | 8/1988 | Lekholm | 607/116 |
| 4,784,161 | 11/1988 | Skalsky et al. | 607/116 |
| 4,796,643 | 1/1989 | Nakazawa et al. | 128/642 |
| 4,848,352 | 7/1989 | Pohndorf et al. | 128/642 |
| 4,892,102 | 1/1990 | Astrinsky | 128/642 |
| 5,293,868 | 3/1994 | Nardella | 128/642 |
| 5,417,208 | 5/1995 | Winkler | 128/642 |

FOREIGN PATENT DOCUMENTS

| | | |
|---|---|---|
| 4112936 | 10/1991 | Germany. |
| 9320750 | 10/1993 | WIPO. |

*Primary Examiner*—Gary F. Paumen
*Assistant Examiner*—Tho Dac Ta
*Attorney, Agent, or Firm*—Hill, Steadman & Simpson

[57] ABSTRACT

An electrode contact device for medical application as a contact device at one end of an electrically insulated conductor or electrode cable for a cardiac pacemaker, has a rotationally symmetrical main body of ceramic material with at least one contact portion of electrically conductive material being formed on the exterior of the main body, and which is in electrical communication with a conductor which can be attached to the contact device. The electrically conductive contact portions on the exterior of the ceramic main body are radially and/or axialy separated from each other and at leaest one of these contact portions is formed by a thin layer of material produced by application of electrically conductive material on a surface area of the main body.

16 Claims, 1 Drawing Sheet

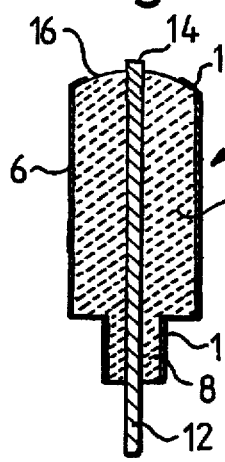
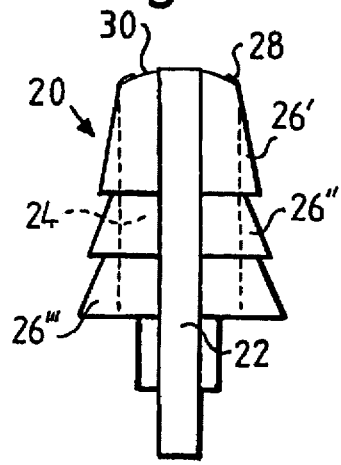
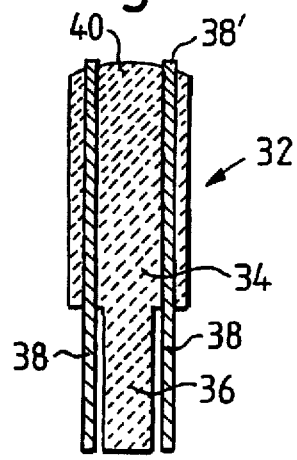
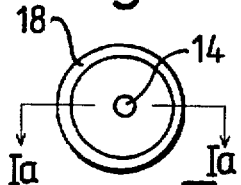
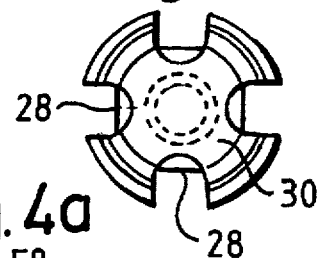
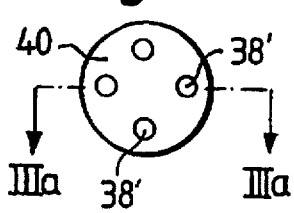
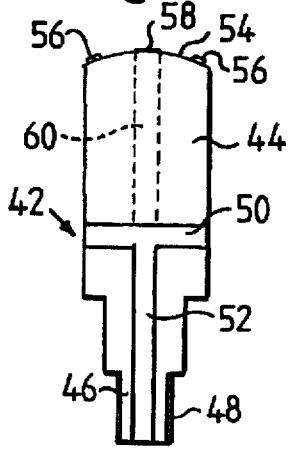
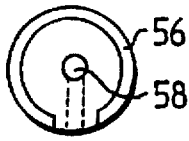
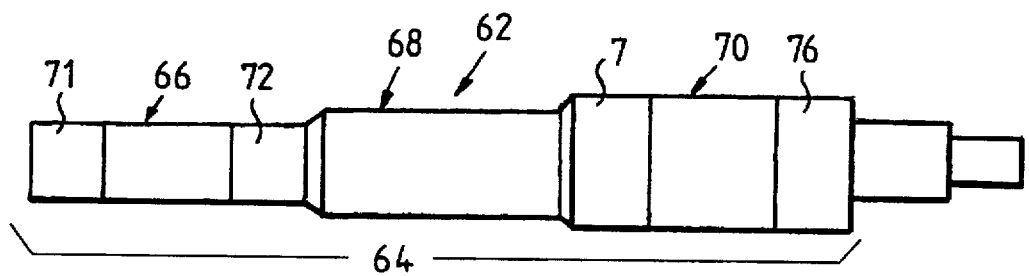

ELECTRODE CONTACT DEVICE, PARTICULARLY AN ELECTRODE CONTACT HEAD, AND AN ELECTRODE ATTACHMENT DEVICE FOR AN ELECTRODE CABLE OF A CARDIAC PACEMAKER, AND A METHOD FOR PRODUCING SUCH AN ELECTRODE CONTACT DEVICE

BACKGROUND OF THE INVENTION

1. Field of the Invention

The present invention relates to an electrode contact device, particlarly an electrode contact head, and an electrode attachment device for an electrode cable of a cardiac pacemaker, and to a method for producing such an electrode contact device.

2. Description of the Prior Art

A contact device of the above general type is intended to be mounted at one end of an insulated electrical conductor or cable, and has the purpose of transmitting electrical signals/electrical current in viroto to and from the implanted conductor and the implanted electrical unit, such as a cardiac pacemaker, or another component attached at the end of the conductor.

A cardiac pacemaker is a battery-operated, electronic impulse generator which can be surgically implanted in a patient whose heart presents dysrhythmia (heart beat irregular or too slow). The pacemaker contains a pulse generator which has the object of stimulating the heart muscle to contract when the heart's own rate of contraction is inadequate. The electrical pulses from such a cardiac pacemaker are transmitted to the heart via one or more thin electrode cables (small diameter, insulated metallic conductors). Each cable has a distal end anchored inside the heart, in the cardiac musculature. The distal end is designed as an electrode contact head with noninsulated contact portions or zones which are in direct electrical contact with the cardiac musculature. When the pacemaker is, for example, a so-caled dual-chamber pacemaker, the pacemaker is in communication with the musculature of the heart via two electrode cables, one of which has its electrode contact head arranged in the right atrium, while the other one has its electrode contact head arranged in the right ventricle. The electrode cables extend into the heart via the subclavian vein. The actual pacemaker is usually surgicaly implanted under the skin, over the left pectoral muscle.

An electrode contact device intended for medical application, and more specifically as a contact device at one end of an electrically insulated conductor or electrode cable for a cardiac pacemaker, is described in German OS 41 12 936. This known contact device has a main body of ceramic material with an exterior on which at least one contact portion is disposed made of electrically conductive material and which is intended to be arranged in electrical communication with a conductor which can be attached to the contact device.

SUMMARY OF THE INVENTION

An object of the present invention is to provide an electrode contact device with a main body which is made of ceramic material and which can constitute a support for the required number of contact portions (in the form of surface areas or zones) made of electrically conductive material, wherein the contact portions can be produced simply, both with the desired design and at the desired positions on the main body.

For electrode contact devices for medical application as implantable electrode contact devices (electrode contact heads and electrode cable attachment devices) in particular, it is of course an important requirement, and consequently an objective, that the size of the respective contact device be made as small as possible.

Another object is to provide an electrode contact device which is well suited for inclusion of those parts, portions and areas/zones of the contact device which provide the mechanical, electrical and physiological functions/properties required of it, so that the device can be manufactured at considerably less cost than has been possible with the technology used to date.

The above objects are achieved in an electrode contact device according to the present invention having a ceramic main body with an exterior on which at least two separate electrically conductive contact portions are disposed, which are situated at different radial distances in relation to a longitudinal axis of the main body, and at least one of these electrically conductive contact portions being formed by an electrically conductive layer of material applied on a surface area of the main body. In practice, it should be possible for any suitable metal to be used as this electrically conductive material. The addition, application or deposition of the material is usually referred to as metallization. As used herein "ceramic material" means inorganic, nonmetallic materials produced by means of a hightemperature reaction. A ceramic which may be suitable in this context is, for example, alumina ($AL_2O_3$).

An electrode contact device intended for a cardiac pacemaker can be either an electrode contact head at one end (the distal end) of an electrode cable or can be an attachment device arranged at the opposite end (the proximal end) of such an electrode cable. In both cases, the ceramic main body can be provided on the outside with two or more electrically conductive contact portions which are radially and/or axially separated from one another, each being formed by a thin layer of material which has been produced by deposition, or another type of surface application, of electrically conductive material on a particular surface area of the main body, which thin layer of material then forms an electrical contact zone on the outside of the contact device.

The thin conductive layer or layers of material, thus constituting contact surfaces on the outside of the contact device, can be formed easily in the desired manner, and can form contact surface patterns or zones at the optimal locations from the point of view of electrical current transmission.

The contact surface areas can be disposed both on the jacket surface of the contact device as well as on its front end surface.

In some cases there is a requirement for the contact device not only to have extensive contact surface areas, but also to have several punctiform contact portions at some region, preferably at the front end surface. An embodiment of the inventive contact device to meet this requirement can then have, for example, has at least one electrically conductive contact element which passes through the ceramic main body in the longitudinal direction thereof, and which is integrated into the ceramic main body. This conductive contact element has an end which projects from the front end surface of the main body, and has an opposite end which projects from a rear of the main body, so as to be connectible to a conductor contained in the electrode cable.

The main body of the contact device will in practice often be designed as a support body which is rotationally symmetrical about its longitudinal axis and which supports the actual conductive surface areas, and may also support one or more projecting pin-like elements serving as contacts which may be present and which are embedded in the main body. Especially in those cases where the contact device is an attachment device arranged at the "pacemaker end" (the proximal end) of an electrode cable, the main body can have two or more axially separated portions with respective diameters of different sizes, with at least one of these portions being provided with a thin electrically conductive layer of material forming a contact zone.

An electrode contact device according to the invention can be produced in many different ways, and using different types of manufacturing techniques. For producing an electrode contact device having at least two separate contact portions, it may be suitable in some cases to use a method according to the method by starting with a core in the form of a main body of ceramic material, on which a layer of electrically conductive material is arranged, after which a layer of ceramic material is arranged on the main body, at least partially overlapping the layer of conductive material. Depending on requirements, it is then possible to apply alternatingly, in a corresponding manner, a layer of conductive material, a layer of ceramic material, and so on.

DESCRIPTION OF THE DRAWINGS

FIGS. 1a and 1b respectively show an axial longitudinal section and an end view from above, of a first embodiment of an electrode contact device according to the invention which is designed as an electrode contact head.

FIGS. 2a and 2b respectively show a side view, and an end view from above, of a second embodiment of an electrode contact head according to the invention.

FIGS. 3a and 3b respectively show an axial longitudinal section, and an end view from above, of a third embodiment of an electrode contact head according to the invention.

FIGS. 4a and 4b respectively show a side view, and an end view from above, of a fourth embodiment of an electrode contact head according to the invention.

FIG. 5 shows, in a side view, a contact device according to the invention designed as an electrode cable attachment device.

DESCRIPTION OF THE PREFERRED EMBODIMENTS

The electrode contact head 2 which is shown in FIGS. 1a and 1b is intended to be arranged in vivo at the "heart muscle end" (the distal end) of an electrode cable whose other end (the "pacemaker end", i.e. the proximal end) is attached to an implanted cardiac pacemaker. FIG. 1a is a sectional view along line Ia—Ia of FIG. 1b. The electrode contact head 2 has an essentially cylindrical main body 4 made of ceramic material. A contact portion 6 formed by a thin layer of metal is arranged on the outside of the main body 4 and surrounds the circumference thereof. The main body 4 has, at the bottom, a narrower shaft portion 8 which can be provided with a metallized surface 10. Passing through the ceramic main body 4, in the longitudinal direction thereof, is a central, axial contact element 12 which is embedded in the main body and whose free end 14 projects a short distance from the end surface 16 of the main body 4. At the outer edge of this end surface 16, the metal layer 6 merges with a circumferential, inwardly directed edge flange 18. The central, axial contact element 12 can be a titanium pin, for example. The metallized contact surfaces 6, 10, 18 of the contact device 2, as well as the contact pin 12, are electrically connected in a conventional manner to their respective conductors in the electrode cable (not shown) which leads to a cardiac pacemaker.

FIGS. 2a and 2b show a second embodiment of an electrode contact head 20 with four axially extending band-shaped surface areas 22, between which the main body 24 is provided with an axial set of barbs 26', 26",26'". The contact surfaces 22 which are designed as metallized areas are provided at the top with inwardly directed end tongues 28 on the end surface 30 of the main body 24.

FIGS. 3a and 3b show an essentially cylindrical electrode contact head 32 whose ceramic main body 34 merges at the bottom with an axial shaft portion 36 of a smaller diameter than the main body 34, with FIG. 3a being a sectional view along line IIIa—IIIa of FIG. 3b. Passing through the ceramic main body 34 in this case are four axially directed contact pins 38 whose free uppermost ends 38'project from the upper end surface 40 of the main body 34. The ceramic main body 34 is shown in this case without any thin conductive surface layer on the jacket surface, although one or more electrically conductive surface layers are intended to be arranged on the main body. In this embodiment as well, the four axial contact pins 38 can be titanium pins, for example.

The electrode contact head 42 shown in FIG. 4 has a rotationally symmetrical main body 44 on whose shaft portion 46 there is a conductive surface layer 48 . On the jacket of the main body 44 there is in this case a ribbon-shaped surface area 50 which annularly runs around the main body 44 and which forms a contact surface area. Connected to this contact surface area there is an axially extending, ribbon-shaped surface area 52. The ceramic main body 44 has in this case, on its upper end surface 54, two contact surface areas 56 and 58 separate from one another. The surface area 56 his the shape of a discontinuous ring, while the surface area 58 has the shape of a radially directed band. The surface area 58 is furthermore in electrical communication with a ribbon-shaped conductor 60 which is integrated or embedded in the ceramic main body 44 and which is indicated by the broken-line contour in FIG. 4a.

A common feature of the four electrode contact heads shown in FIGS. 1–4 is that they are multi-pole contact heads.

Finally, the electrode contact device shown in FIG. 5, is in the form of an end attachment device 62 intended to be arranged at the "pacemaker end", i.e. the proximal end, of an electrode cable at whose other end (the distal end) there is an electrode contact head. The main body 64 of the end attachment device 62 again is of a ceramic material, and the main body 64 is, as can be seen, a cylindrical body with three axially separated sections or portions 66, 68 and 70 with respective diameters increasing in steps. The portion 68 is in this case shown with two ribbon-like contact surfaces or contact zones 71 and 72 which extend completely around the circumference, while the portion 68 of the main body has no electrically conductive surface layer. In this case, the portion 70 of the main body also has two axially separated contact zones 74 and 76. Instead of two contact zones, it is alternatively possible for the portions 68 and 70 of the main body each to have a single, continuous contact surface layer. If necessary, the portion 68 of the main body 64 could also be provided with some type of conductive metal surface layer.

Although modifications and changes may be suggested by those skilled in the art, it is the intention of the inventor to embody within the patent warranted hereon all changes and modifications as reasonably and properly come within the scope of his contribution to the art.

I claim as my invention:

1. An electrode contact device for an implantable medical apparatus attachable to an end of an electrically insulated conductor, comprising:

a main body of ceramic material having a longitudinal axis and an exterior; and at least two separate electrically conductive contact portions on said exterior of said main body at respectively different radial spacings relative to said longitudinal axis, at least one of said electrically conductive contact portions consisting of an electrically conductive layer of material applied on, and completely in contact with, a surface area of said exterior of said main body.

2. An electrode contact device as claimed in claim 1 wherein said main body comprises an electrode contact head adapted for electrical connection at one end of said electrically insulated conductor.

3. An electrode contact device as claimed in claim 1 wherein said main body comprises means for attaching said electrically insulated conductor to an implanted medical stimulator.

4. A contact device as claimed in claim 1 wherein at least one of said electrically conductive contact portions comprises a ribbon-shaped layer of electrically conductive material extending parallel to a longitudinal direction of said main body.

5. A contact device as claimed in claim 1 wherein said main body comprises a rotationally symmetrical body relative to a longitudinal axis of said main body and wherein said electrically conductive contact portions comprise two contact ribbons separated from each other and extending parallel to said longitudinal axis along at least a part of a longitudinal extent of said rotationally symmetrical body.

6. A contact device as claimed in claim 1 comprising an electrically conductive contact element proceeding through said main body along said longitudinal axis of said main body and integrated in said main body, said contact element having a first end projecting from a front end surface of said main body forming one of said contact portions and having a second, opposite end projecting from a rear of said main body and adapted for electrical connection to said electrically insulated conductor.

7. A contact device as claimed in claim 1 wherein said main body comprises a cylindrical body having at least two axially separated portions having respective diameters of different sizes, with at least one of said axially separated portions having one of said electrically conductive contact portions thereon.

8. A contact device as claimed in claim 1 wherein said electrically conductive contact portions respectively consist of ribbon-shaped thin electrically conductive material on said exterior of said main body extending transversely to a longitudinal direction of said main body.

9. A contact device as claimed in claim 8 wherein said ribbon-shaped material completely surrounds a circumference of said main body.

10. A contact device as claimed in claim 8 wherein said ribbon-shaped material partially surrounds a circumference of said main body.

11. A contact device as claimed in claim 1 wherein said main body has a front end surface, and wherein at least one of said electrically conductive contact portions comprises a thin layer of material on said front end surface.

12. A contact device as claimed in claim 11 wherein said electrically conductive contact portion on said front end surface of said main body comprises two separate layers of material applied on said main body.

13. A method for producing an electrode contact device having at least two separate contact portions, comprising the steps of:

(a) providing a main body of ceramic material;

(b) arranging a layer of electrically conductive material on said main body;

(c) arranging a layer of ceramic material on said main body at least partially overlapping said layer of conductive material; and repeating steps (b) and (c) a selected number of times for producing a selected number of contact portions on said main body.

14. An electrode contact device for implantable medical apparatus attachable to an end of an electrically insulated conductor, comprising:

a main body of ceramic material having a longitudinal axis; and a plurality of electrically conductive contact elements proceeding through said main body parallel to said longitudinal axis and integrated in said main body, each electrically conductive contact element having a first end projecting from a front end surface of said main body and forming a contact portion and having a second, opposite end projecting from a rear of said main body and adapted for electrical connection to said electrically insulated conductor, said main body electrically insulating the contact portions from each other.

15. A contact device as claimed in claim 14 wherein said plurality of electrically conductive contact elements comprises four said electrically conductive contact elements.

16. A contact device as claimed in claim 14 wherein said electrically conductive contact elements and said contact portions are integrated in said main body radially symmetrically distributed around said longitudinal axis.

* * * * *